United States Patent [19]

Pereira

[11] Patent Number: 4,981,845

[45] Date of Patent: Jan. 1, 1991

[54] COSMETIC COMPOSITION

[75] Inventor: Mavis C. Pereira, Lower Bebington, England

[73] Assignee: Chesebrough Pond's U.S.A. Co., Division of Conopco, Inc., Greenwich, Conn.

[21] Appl. No.: 399,643

[22] Filed: Aug. 25, 1989

[30] Foreign Application Priority Data

Sep. 9, 1988 [GB] United Kingdom ................ 8821129

[51] Int. Cl.$^5$ ...................... A61K 31/19; A61K 31/20
[52] U.S. Cl. .................................... 514/557; 514/558; 514/941
[58] Field of Search ........................ 514/557, 558, 941

[56] References Cited

U.S. PATENT DOCUMENTS 4,424,234  1/1984  Alderson et al. .................. 514/558
4,699,924 10/1987  Durrant et al. .................... 514/558

OTHER PUBLICATIONS

Chemical Abstracts 100: 215,284q (1974).

Primary Examiner—Leonard Schenkman
Attorney, Agent, or Firm—Milton L. Honig

[57] ABSTRACT

An emulsion suitable for topical application to human skin or hair comprises, in addition to water from 0.01 to 20% by weight of a skin benefit ingredient, preferably a 2-hydroxyalkanoic acid having from 3 to 20 carbon atoms, or a salt thereof; from 0.1 to 20% by weight of polyoxyethylene-21-stearyl ether, as a principle emulsifier and from 0.5 to 70% by weight of an emollient oil.

10 Claims, No Drawings

COSMETIC COMPOSITION

FIELD OF INVENTION

The invention relates to emulsions which are suitable for topical application to skin or hair, more particularly to emulsions comprising a 2-hydroxyalkanoic acid or a salt thereof or other skin benefit agents.

BACKGROUND AND PRIOR ART

The use of 2-hydroxyoctanoic acid in products for topical application to human skin has been proposed in EP-A 0 007 785 (Unilever). There remains, however, a problem in delivering this acid to subcutaneous regions of the skin, where its benefit of increasing the extensibility of stratum corneum is maximised.

An attempt has subsequently been made, as described in EP-A-0 117 080 (Unilever), to improve the delivery of amphiphylic compounds such as 2-hydroxyoctanoic acid by the use of an emulsifier having an average HLB value of from 5 to 11, which is capable with water of forming a gel phase having an X-ray reflection of from 0.37 to 0.44, and which permits substantially no co-crystallisation with the amphiphylic compound. Although improved delivery of 2-hydroxyoctanoic acid has been demonstrated with compositions based on the emulsifier system disclosed in this reference, their shelf life is limited, in that syneresis tends to occur after storage at 45° C. (the normal maximum storage temperature for testing stability) for only a few weeks. Such limitations as to storage stability virtually rule out the possibility of employing such systems in products where many weeks or months may elapse during storage prior to sale or prior to use by the consumer.

We have now discovered that by selecting a special emulsifier not previously proposed for use with 2-hydroxyoctanoic acid and related substances, that emulsions can be prepared which are completely stable during storage at 45° C. for at least 12 months, or longer at lower storage temperatures, and which also show excellent freeze-thaw stability following cooling to −22° C., thus providing an answer to a long felt need for superior storage stability characteristics. Furthermore, emulsions containing certain other skin benefit agents in place of or in addition to 2-hydroxyalkanoic acids such as 2-hydroxyoctanoic acid, also benefit from exceptional storage stability when using the special emulsifier.

DEFINITION OF THE INVENTION

Accordingly, the invention provides an emulsion suitable for topical application to human skin or hair, which comprises in addition to water:

(i) from 0.01 to 20% by weight of a skin benefit ingredient chosen from:
Retinoic acid
Retinyl palmitate
Ascorbic acid
Ascorbyl palmitate
Tocopherol
Tocopherol acetate
Pyroglutamic acid and salts thereof
Amino acids
Sunscreens
Hyaluronic acid and salts thereof
Perfluoropolyether
Hydrocortisone acetate and
a 2-hydroxyalkanoic acid having from 3 to 20 carbon atoms, or a salt thereof; and
mixtures thereof;

(ii) from 0.1 to 20% by weight of polyoxyethylene-21-stearyl ether as a principle emulsifier; and (iii) from 0.5 to 70% by weight of an emollient oil.

DISCLOSURE OF THE INVENTION

The Emulsion

The emulsion according to the invention will normally contain an aqueous phase and an oily phase and will comprise a selected skin benefit ingredient, a special emulsifier and an emollient oil.

The emulsion preferably possesses a continuous aqueous phase in which case it is an oil-in-water emulsion, the aqueous phase comprising from 98 to 60% by volume and the oily phase from 2 to 40% by volume of the emulsion.

Alternatively, the emulsion can possess a continuous oily phase, in which case it is a water-in-oil emulsion, the aqueous phase usually comprising from 25 to 70% by volume and the oily phase from 75 to 30% by volume of the emulsion. However, the emulsion can also be a high internal phase water-in-oil emulsion, in which case the aqueous phase can comprise up to 98% by volume of the emulsion, the oily phase then forming as little as 2% by volume of the emulsion.

The form of the emulsion, whether oil-in-water or water-in-oil, will largely depend upon the average HLB value of the emulsifier(s) which is employed, values greater than 8 generally giving rise to oil-in-water emulsions and values of up to 8 generally giving rise to water-in-oil emulsions.

The Emulsion Ingredients (i) The skin benefit ingredient

The emulsion according to the invention comprises a skin benefit ingredient chosen from
Retinoic acid
Retinyl palmitate
Ascorbic acid
Ascorbyl palmitate
Tocopherol
Tocopherol acetate
Pyroglutamic acid and salts thereof
Amino acids
Sunscreens
Hyaluronic acid and salts thereof
Perfluoropolyether
Hydrocortisone acetate and
a 2-hydroxyalkanoic acid having from 3 to 20 carbon atoms, or a salt thereof; and
mixtures thereof;

The emulsion can also comprise a mixture of two or more skin benefit ingredients. Particularly preferred examples of amino acids include:
glycine
alanine
valine
leucine
isoleucine
phenylalanine
tyrosine
proline
hydroxyproline
serine
threonine cysteine
cystine
methionine
tryptophan
aspartic acid
glutamic acid
arginine
lysine, and
histidine.

The amount of amino acid that can be employed in accordance with the invention will normally be from 0.01 to 20%, preferably from 0.1 to 10% by weight of the emulsion. Particularly preferred examples of sunscreen active ingredients include:

p-Aminobenzoic acid
Ethyl dihydroxypropyl p-aminobenzoic acid (such as Amerscreen P)
Glyceryl p-aminobenzoic acid (such as Escalol 106)
2,4-Dihydroxy benzophenone (such as Uvinul 400)
2-Ethoxyethyl-p-methoxycinnamate (such as Giv Tan F)
Di-ethanolamine p-methoxycinnamate (such as Parsol Hydro)
2-Ethylhexyl salicylate (such as Sun Arome WMO)
Homomethyl salicylate (such as Filtrosol A)
2-Phenylbenzimidazole-5-sulphonic acid (such as Eusolex 232)
Octyl methoxycinnamate (such as Parsol MCX).
3-(4-Methylbenzylidine) camphor (such as Eusolex 6300)
2-Hydroxy-4-methoxy benzophenone (such as Eusolex 4360)
Butylmethoxydibenzoylmethane (such as Parsol 1789)
4-isopropyl dibenzoylmethane (such as Eusolex 8020).

The amount of the sunscreen active ingredient that can optionally be employed in accordance with the invention, as a therapeutically effective amount, will normally be from 0.01 to 10%, preferably from 0.1 to 5% and most preferably from 1 to 5% by weight of the emulsion.

Particularly preferred examples of 2-hydroxyalkanoic acids include 2-hydroxypropanoic acid, 2-hydroxyhexanoic acid and 2-hydroxyoctanoic acid. Further examples include 2-hydroxy-N-butanoic acid, 2-hydroxydecanoic acid, 2-hydroxydodecanoic acid and 2-hydroxyoctadecanoic acid.

Examples of salts of the above 2-hydroxyalkanoic acids are the sodium, potassium and triethanolamine salts, although it is to be understood that other metallic, ammonium or alkanolammonium salts are useful.

The emulsion according to the invention can comprise mixtures of 2-hydroxyalkanoic acids and/or salts and/or an acid soap complex thereof.

The most preferred 2-hydroxyalkanoic acid is 2-hydroxyoctanoic acid or its acid soap complex having the empirical formula

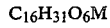

$C_{16}H_{31}O_6M$ where M is a cation chosen from sodium, potassium and ammonium.

The amount of skin benefit ingredient present in the emulsion according to the invention is usually from 0.01 to 20%, preferably from 0.1 to 10% by weight of the emulsion.

(ii) The Principle Emulsifier

The emulsion according to the invention comprises as the principle emulsifier polyoxyethylene-21-stearyl ether, also known as polyoxyethylene-21-stearyl alcohol, an example of which is Brij 721 (available from ICI). This emulsifier has an HLB value of about 15.5 and if used alone will yield an oil-in-water emulsion.

The amount of polyoxyethylene-21-stearyl ether present in the emulsion according to the invention is usually from 0.1 to 20%, preferably from 0.5 to 10% by weight of the emulsion.

(iii) The Emollient Oil

The emulsion according to the invention comprises an emollient oil, that is an oily substance that is substantially insoluble, or only slightly soluble in water, and which usually constitutes the major ingredient of the oily phase of the emulsion.

Examples of emollient oils include the following:

1. Hydrocarbon oils and waxes: examples of which include, mineral oil, petrolatum, paraffin, ozokerite, microcrystalline wax, polyethylene and perhydrosqualene (squalane).

2. Silicone oils: examples of which include, dimethyl polysiloxanes, methylphenyl polysiloxanes.

3. Triglyceride esters: examples of which include, vegetable and animal fats and oils, such as caprylic and capric triglycerol (available as Migliol 812), wheatgerm oil, apricot kernel oil, avocado oil, sunflower seed oil, arnica oil, evening primrose oil and jojoba oil.

4. Acetoglyceride esters: examples of which include, acetylated monoglycerides.

5. Alkyl esters: examples of which include, methyl, isopropyl, and butyl esters of fatty acids; hexyl laurate, isohexyl laurate, isopropyl myristate, isopropyl palmitate, decyl oleate, isodecyl oleate, hexadecyl (isocetyl) stearate, diisopropyl adipate, diisohexyl adipate, dihexadecyl adipate, diisopropyl sebacate, lauryl lactate, myristyl lactate, and cetyl lactate.

6. Alkenyl esters: examples of which include, oleyl myristate, oleyl stearate, and oleyl oleate.

7. Fatty acids: examples of which include, lauric, myristic, palmitic, stearic, isostearic, hydroxystearic, oleic, linoleic, linolenic, γ-linolenic, ricinoleic, arachidic, behenic, erucic, and lanolin acids.

8. Fatty alcohols: examples of which include, lauryl, myristyl, cetyl, hexadecyl (isocetyl), stearyl, isostearyl, hydroxystearyl, oleyl, ricinoleyl, behenyl and erucyl alcohols, and 2-octyl dodecanol.

9. Fatty alcohol ethers: examples of which include, ethoxylated lauryl, cetyl, stearyl, isostearyl, oleyl, and lanolin alcohols; and cholesterol; propoxylated cetyl, oleyl, and lanolin alcohols; and also polypropylene-15-stearyl ether.

10. Ether-esters: examples of which include, fatty acid esters of ethoxylated fatty alcohols.

11. Lanolin and lanolin derivatives: examples of which include, lanolin, lanolin oil, lanolin wax, lanolin alcohols, lanolin fatty acids and acetylated lanolin derivatives.

12. Wax esters: examples of which include, lanolin (de-oiled wax fraction), beeswax, spermaceti, myristyl myristate, stearyl stearate.

13. Beeswax derivatives: examples of which include, polyoxyethylene sorbitol beeswax. These are reaction products of beeswax with ethoxylated sorbitol of varying ethylene oxide content, forming a mixture of ether-esters.

14. Vegetable waxes: examples of which include, carnauba, candelilla.

15. Phopholipids: examples of which include, lecithin and derivatives.

16. Sterols: Cholesterol, cholesterol fatty acid esters.

The amount of emollient oil present in the emulsion according to the invention is usually from 0.5 to 70%, preferably from 1 to 60% by weight of the emulsion.

Other emulsion ingredients (i) Secondary Emulsifiers

The emulsion according to the invention can also comprise one or more secondary emulsifiers, in addition the principle emulsifier polyoxyethylene-21-stearyl ether.

Examples of secondary emulsifiers include:

|  | HLB value |
|---|---|
| BRIJ 72 (Polyoxyethylene-2-stearyl ether) | 4.9 |
| BRIJ 52 (Polyoxyethylene-2-cetyl ether) | 5.3 |

The presence of a secondary emulsifier can result in the formation of a water-in-oil emulsion, if the average HLB of all emulsifiers present does not exceed 8. The preferred emulsions according to the invention are, however oil-in-water emulsions.

The amount of secondary emulsifiers that optionally can be present in the emulsion according to the invention is up to 20%, preferably from 0.1 to 10% by weight of the emulsion.

(ii) Thickeners

The emulsion according to the invention can also optionally comprise a thickener, examples of which include:
xanthan gum, such as Rhodopol 23,
aluminum starch octenylsuccinate, such as Dry Flo starch,
carboxyvinyl polymer, such as Carbopol 938, 940 & 941
carboxymethyl cellulose, and
hydroxypropylmethyl cellulose.

The amount of thickener that optionally can be present in the emulsion according to the invention will depend upon which thickener is chosen, the amount being that conventionally employed as recommended by the respective manufacturer. Generally, the amount of thickener will be up to 10%, preferably from 0.1 to 5% by weight of the emulsion.

(iii) Skin Delivery Enhancers

The emulsion according to the invention can also optionally comprise one or more substances to enhance delivery of the skin benefit ingredient to the stratum corneum. Examples of skin delivery enhancers, which can function in a variety of ways, include:
2-methyl propan-1-ol
Propane-1,2-diol
Ethyl-2-hydroxypropanoate
Hexane-2,5-diol
POE (2) ethyl ether
Di (2-hydroxypropyl) ether
Pentane-2,4-diol
POE (2) methyl ether
Tetrahydrofuran
Butane-1,3-diol
Propylene glycol dipelargonate
Octyl alcohol
POE ester of oleyl alcohol
Oleyl alcohol
Lauryl alcohol
Dioctyl adipate
Dicapryl adipate
Diisopropyl adipate
Diisopropyl sebacate
Dibutyl sebacate
Diethyl sebacate
Dimethyl sebacate
Dioctyl sebacate
Dibutyl suberate
Dioctyl azelate
Dibenzyl sebacate
Dibutyl phthalate
Dibutyl azelate
Ethyl myristate
Dimethyl azelate
Butyl myristate
Dibutyl succinate
Didecyl phthalate
Decyl oleate
Ethyl caproate
Ethyl salicylate
Ethyl laurate
2-ethyl-hexyl pelargonate
Isopropyl isostearate
Butyl laurate
Benzyl benzoate
Butyl benzoate
Hexyl laurate
Ethyl caprate
Ethyl caprylate
Butyl stearate
Benzyl salicylate
Glycerol.

The amount of skin delivery enhancer, when employed in accordance with the invention, will normally be from 0.1 to 50%, preferably from 0.5 to 25% and most preferably from 0.5 to 15% by weight of the emulsion.

(iv) Perfume

The emulsion according to the invention can also optionally comprise a perfume in an amount sufficient to make the emulsion acceptable to the consumer and pleasant to use. Usually, the perfume when present will form from 0.01 to 10% by weight of the emulsion.

(v) Further optional ingredients

The emulsion according to the invention can also optionally comprise further ingredients in addition to those already described, such as colourants, whiteners, preservatives, antioxidants, or aerosol propellants, in amounts which are conventional in the cosmetics art.

pH

The emulsion according to the invention should normally have a pH value of from 3 to 7, preferably from 3.8 to 5 and ideally from 4 to 4.5.

When the emulsion is an oil-in-water emulsion, the continuous phase being the aqueous phase, then the pH value can be measured directly from a pH electrode placed in the emulsion.

When the emulsion is a water-in-oil emulsion, the continuous phase being the oily phase, then direct pH measurement of the emulsion is not possible. In this case, the pH value refers to that of the aqueous phase before emulsifying in the presence of the oily phase.

PRODUCT FORMS AND PACKAGING

The topical skin treatment emulsion of the invention can be formulated as a fluid, for example in a product such as a lotion, with or without an applicator such as a roll-ball applicator, or a propellant-driven aerosol device or a container fitted with a pump to dispense the composition, for example as a mousse or simply for storage in a non-deformable bottle or squeeze container. Alternatively, the composition of the invention may be solid or semi-solid, for example a cream or ointment, for use in conjunction with a suitable applicator, or simply for storage in a tube or lidded jar.

More particularly, the viscosity of the emulsion will determine whether it is a lotion or a cream. For example, when the viscosity of the emulsion is measured using the Brookfield Viscometer (10 rpm, measured at 20° C. using spindles A to D as appropriate) then the following viscosity values provide a guide to the nature of the emulsion.

| Viscosity (mPas) | Description of emulsion |
|---|---|
| up to 2,000 | milk |
| 2,000 to 5,000 | thin lotion |
| 5,000 to 8,000 | normal pourable lotion |
| 8,000 to 10,000 | thick lotion* |
| 10,000 to 15,000 | thin cream |
| 15,000 to 30,000 | normal cream |
| 30,000 to 100,000 | thick cream |

*dispensible from a squeeze container.

The invention accordingly also provides a closed container containing a cosmetically acceptable composition as herein defined.

PREPARATION AND PRODUCT FORM OF THE EMULSION

The emulsion of the invention can be prepared in the form of a lotion, cream, gel, ointment, solid stick or aerosol, or in any other form suited to administration topically to human skin.

Accordingly, the invention also provides a process for the preparation of an emulsion suitable for topical application to human skin or hair, which process comprises the steps of:

i. preparing an aqueous phase, buffered to a pH value of from 3 to 7, comprising a skin benefit ingredient as herein defined, preferably a 2-hydroxyalkanoic acid or derivative thereof having from 3 to 20 carbon atoms, together with further water-soluble or water-dispersible ingredients as necessary.

ii. preparing an oily phase comprising emollient oil and polyoxyethylene-21-stearyl ether as emulsifier, together with other oil soluble ingredients;

iii. adding the oily phase preheated to a temperature of at least 70° C. to the aqueous phase, also preheated to a temperature of at least 70° C., with high shear mixing to form an emulsified mixture;

iv. cooling the emulsified mixture to a temperature of from 35° to 50° C. and adding the aqueous buffer with low shear mixing;

v. cooling to a temperature of not greater than 35° C. and adding preservatives and perfume as required with further mixing;

to obtain emulsion as herein defined.

EVIDENCE TO DEMONSTRATE SUPERIOR STORAGE STABILITY OF EMULSIONS

As has been stated earlier, the emulsions of the invention exhibit superior stability during storage at 45° C. to any other emulsion containing skin benefit ingredients, such as 2-hydroxyalkanoic acids.

This superiority was demonstrated using a formulation comprising the principle emulsifier, namely, polyoxyethylene-21-stearyl ether, compared with two similar formulations, in which this principle emulsifier had been replaced by other emulsifiers.

The basic lotion formulation contained the following ingredients

| | % w/w |
|---|---|
| 2-hydroxy alkanoic acids | |
| 2-hydroxy propanoic acid | 4.0 |
| 2-hydroxy octanoic acid | 1.0 |
| Emulsifier as selected* | 1.8 |
| Emollient oils | |
| lanolin derivative | 0.95 |
| wheatgerm oil | 0.05 |
| isopropyl myristate | 1.0 |
| cetyl palmitate | 2.0 |
| wax | 2.0 |
| fatty alcohol | 1.2 |
| silicone oil | 6.0 |
| Thickeners | |
| aluminium starch octenyl succinate | 3.0 |
| xanthan gum | 0.1 |
| Delivery enhancer | |
| butane-1,3-diol | 9.45 |
| Other ingredients | |
| whitener | 0.15 |
| preservatives | 0.36 |
| water | to 100 |

Three lotions were prepared based on the above formula: these were identical except for the emulsifiers which were as follows:

| Lotion | Emulsifier* |
|---|---|
| A | Brij 58 (polyoxyethylene-20-cetyl ether) |
| B | Brij 78 (polyoxyethylene-20-stearyl ether) |
| C | Brij 721 (polyoxyethylene-21-stearyl ether) |

Results

The following results were obtained after storage:
(i) Stability data

The results of storage tests at −22° C.(4 F/T cycles), 20° C., 35° C. and 45° C. on the three basic lotion models are given in Table 1.

TABLE 1

Stability Data for Lotion Models

| Lotion | Freeze-Thaw Cycles (× 4) at −22° C. | 20° C. | 35° C. | 45° C. |
|---|---|---|---|---|
| A | Stable after 4 × | Stable for 18 months | Stable for 1 mth then oil on surface | Stable for 1 mth then separated |
| B | Stable after 4 × | Stable for 18 months | Stable for 3 mths then separated | Stable for 2 mths then separated |
| C | Stable after 4 × | Stable for 20 months (storage ongoing) | Stable for 13 months | Stable for 13 months |

Table 1 shows that all three lotions survived four freeze-thaw cycles at −22° C. With regard to the storage data, there appears to be a trend in the stability conferred by the emulsifiers on the o/w emulsions such that, that containing Brij 721 was clearly far more stable, even when stored at 45° C., than those containing either Brij 78 or Brij 58.

This confirmed that Lotion C in accordance with the invention exhibited unexpected superior storage characteristics.

(ii) Microstructure of Lotions

The microstructure of each lotion was studied 24 hours after preparation, and then after 3 months storage at 20° C., and after 6 months storage at 20° C. The results obtained are given in Table 2.

TABLE 2

| | Results from Microstructure Studies (magnification × 100) | | |
|---|---|---|---|
| Lotion | 24 hr after preparation | After 3 mths storage at 20° C. | After 6 mths storage at 20° C. |
| A | Emulsion appeared stable | Flocculation and some coalescence | Islets of coalesced oil droplets; some phase separation. |
| B | Emulsion appeared stable | Flocculation of oil droplets | Coalescence of oil droplets |
| C | Emulsion appeared stable. Particle size smaller than for Lotions A or B | Microstructure unaltered. | No gross changes in microstructure and no evidence of flocculation or coalscence. |

The microstructure results reported above provide further evidence to support the finding that the most stable lotion was Lotion C in accordance with the invention.

(iii) Rheology of lotions

All three lotions A, B and C showed some thickening during storage see Table 3. Of the three, Lotion C showed the least change after six months storage. The results obtained are given in Table 3.

TABLE 3

| | Viscosity Data using Brookfield Viscometer (at 20° C., 10 rpm using Spindle B) | |
|---|---|---|
| | VISCOSITY | |
| Lotions | 24 hr after preparation (mPas) | After 6 mths storage at 20° C. (mPas) |
| A | 4200 | 6200 |
| B | 1200 | 8400 |
| C | 6000 | 7200 |

The viscosity measurements reported above indicate that Lotion C, whose initial viscosity was ideal to enable it to be used as a normal pourable lotion, showed the least change in viscosity during prolonged storage, whereas the comparative Lotions A and B, both of which were too thin for use 24 hours after preparation, showed unacceptable increases in viscosity during storage.

Evidence to Demonstrate Increase in Extensibility of Stratum Corneum

The ability of the emulsion according to the invention to enhance the delivery to skin of 2-hydroxyoctanoic acid, as an example of the 2-hydroxy alkanoic acids, or salts thereof, as herein defined, was measured in terms of the increase in extensibility of heat-separated guinea pig foot pad stratum corneum following contact with the emulsion, as compared with another emulsion which did not contain polyoxyethylene-21-stearyl ether.

In this experiment, pieces of guinea pig foot pad stratum corneum, equilibrated at a relative humidity of 64%, were immersed in each emulsion or control for 3 hours at 20° C., and then removed, blotted dry and re-equilibrated at the same relative humidity. The extensibility of each piece of guinea pig foot pad stratum corneum was measured before and after this treatment in an extensiometer according to the method described in EP-A-0 007 785.

Results

The results of this experiment are tabulated below:

TABLE 4

| | In Vitro Extensibility Data (20° C., 64% RH) | |
|---|---|---|
| Lotion | Extensibility ratio | (± 2 Standard errors) |
| A | 6.6 | (+1.8) |
| C | 8.1 | (+1.4) |

The above results indicate that there is an 23% increase in extensibility in vitro when the principle emulsifier, as herein defined, is employed (i.e. Lotion C in accordance with the invention), compared with control Lotion A containing an ordinary emulsifier. This confirms significantly enhanced delivery to the stratum corneum of 2-hydroxyoctanoic acid using the emulsion of the invention as compared with a control emulsion.

EXAMPLES

The invention is further illustrated by the following examples.

EXAMPLE 1

This example illustrates an oil-in-water skin cream according to the invention.

| | % w/w |
|---|---|
| Skin benefit ingredients | |
| 2-hydroxypropanoic acid | 4.0 |
| 2-hydroxyoctanoic acid | 1.0 |
| Principle emulsifier polyoxyethylene-21-stearyl ether | 2.4 |
| Secondary emulsifier polyoxyethylene-2-stearyl ether | 2.6 |
| Emollient oils | |
| polyoxypropylene-15-stearyl ether | 8.0 |
| fatty alcohol | 4.0 |
| silicone oil | 0.1 |
| Delivery enhancer butane-1,3-diol | 5.0 |
| Other ingredients | |
| preservative | 0.36 |
| pH adjustant | 3.36 |
| perfume | 0.1 |
| water | 69.08 |
| | 100.00 |

The cream had a pH value of 4.

EXAMPLE 2

This example illustrates an oil-in-water skin lotion according to the invention.

| | % w/w |
|---|---|
| Skin benefit ingredients | |
| 2-hydroxy propanoic acid | 4.0 |
| 2-hydroxy octanoic acid | 1.0 |
| Principle emulsifier polyoxyethylene-21-stearyl ether | 1.8 |
| Emollient oils | |
| lanolin derivative | 0.95 |
| wheatgerm oil | 0.05 |

-continued

| | % w/w |
|---|---|
| isopropyl myristate | 1.0 |
| cetyl palmitate | 2.0 |
| wax | 2.0 |
| fatty alcohol | 1.2 |
| silicone oil | 6.0 |
| Thickeners | |
| Aluminium starch octenyl succinate | 3.0 |
| xanthan gum | 0.1 |
| Delivery enhancer | 9.45 |
| butane-1,3-diol | |
| Other ingredients | |
| whitener | 0.15 |
| preservatives | 0.36 |
| pH adjustant | 3.36 |
| perfume | 0.1 |
| water | 63.48 |
| | 100.00 |

The lotion had a pH value of 4.

| Viscosity: Brookfield Viscometer, 10 rpm, Spindle B measured at 20° C. | | |
|---|---|---|
| Storage time: | 24 hrs | 6 months |
| Viscosity (in mPas) | 6000 | 7200 |

EXAMPLE 3

This example illustrates on oil-in-water fluid skin cream according to the invention.

| | % w/w |
|---|---|
| Skin benefit ingredients | |
| 2-hydroxy propanoic acid | 4.0 |
| 2-hydroxy octanoic acid | 1.0 |
| Principle emulsifier | 1.8 |
| polyoxyethylene-21-stearyl ether | |
| Emollient oils | |
| lanolin derivative | 0.95 |
| wheat germ oil | 0.05 |
| cetyl palmitate | 2.0 |
| isopropyl myristate | 1.0 |
| wax | 3.0 |
| fatty alcohol | 1.2 |
| silicone oil | 5.0 |
| Thickeners | |
| aluminium starch octenyl succinate | 3.0 |
| xanthan gum | 0.1 |
| Delivery enhancer | 9.45 |
| butane-1,3-diol | |
| Other ingredients | |
| whiteners | 0.15 |
| preservative | 0.36 |
| pH adjustant | 3.36 |
| perfume | 0.1 |
| water | 63.48 |
| | 100.00 |

The emulsion had a pH value of 4.

| Viscosity: Brookfield Viscometer, 10 rpm, Spindle B measured at 20° C. | | |
|---|---|---|
| Storage time: | 24 hrs | 13 weeks |
| Viscosity (mPas) | 5800 | 22,000 |

EXAMPLE 4

This example illustrates an oil-in-water skin cream according to the invention.

| | % w/w |
|---|---|
| Skin benefit ingredients | |
| 2-hydroxy propanoic acid | 4.0 |
| 2-hydroxyoctanoic acid | 1.0 |
| Principle emulsifier | 0.94 |
| polyoxyethylene-21-stearyl ether | |
| Secondary emulsifier | 0.86 |
| polyoxyethylene-2-stearyl ether | |
| Emollient oils | |
| lanolin derivative | 0.95 |
| wheat germ oil | 0.05 |
| isopropyl myristate | 1.0 |
| cetyl palmitate | 2.0 |
| ozokerite wax | 3.0 |
| fatty alcohol | 1.2 |
| silicone oil | 5.0 |
| Thickeners | |
| aluminium starch octenyl succinate | 3.0 |
| xanthan gum | 0.1 |
| Delivery enhancer | 9.45 |
| butane-1,3-diol | |
| Other ingredients | |
| whitener | 0.15 |
| preservatives | 0.36 |
| pH adjustant | 3.36 |
| perfume | 0.1 |
| water | 63.48 |
| | 100.00 |

The cream had a pH value of 4.

| Viscosity: Brookfield Viscometer, 10 rpm, Spindle D measured at 20° C. | |
|---|---|
| Storage time: | 24 hrs |
| Viscosity (mPas) | 50,000 |

EXAMPLE 7

This example illustrates an oil-in-water emulsion according to the invention.

| | % w/w |
|---|---|
| Skin benefit ingredients | |
| retinyl palmitate | 0.10 |
| octyl methoxy cinnamate | 3.00 |
| butylmethoxydibenzoylmethane | 1.50 |
| Emulsifiers | |
| polyoxyethylene-21-stearyl ether | 2.40 |
| polyoxyethylene-2-stearyl ether | 2.60 |
| Emollient oils | |
| wheatgerm oil | 0.10 |
| caprylic/capric triglycerides | 5.00 |
| silicone oil | 2.50 |
| evening primrose oil | 0.40 |
| Delivery enhancer | 5.00 |
| glycerol | |
| Other ingredients | |
| allantoin | 0.50 |
| preservatives | 0.36 |
| perfume | 0.15 |
| water | to 100% |

The emulsion will have a pH value of from 3 to 7.

EXAMPLE 8

This example illustrate an oil-in-water emulsion according to the invention.

|  | % w/w |
| --- | --- |
| Skin benefit ingredients | |
| L-proline | 0.1 |
| octyl methoxycinnamate | 1 |
| Emulsifiers | |
| polyoxyethylene-21-stearyl ether | 3 |
| polyoxyethylene-2-stearyl ether | 2 |
| Emollient oils | |
| stearyl alcohol | 1 |
| polyoxypropylene-15-stearyl ether | 10 |
| silicone oil | 0.5 |
| evening primrose oil | 1 |
| Delivery enhancer | 4 |
| propane-1,4-diol | |
| Other ingredients | |
| preservative and perfume | qs |
| water | to 100 |

This emulsion will have a pH value of from 3 to 7.

I claim:

1. An emulsion suitable for topical application to human skin or hair, which comprises in addition to water:
   i. from 0.01 to 20% by weight of a skin benefit ingredient selected from the group consisting of: 2-hydroxyalkanoic acid having from 3 to 20 carbon atoms and salts thereof; and
   ii. from 0.1 to 20% by weight of polyoxyethylene-21-stearyl ether, as a principle emulsifier; and
   iii. from 0.5 to 70% by weight of an emollient oil.

2. The emulsion of claim 1, wherein the 2-hydroxyalkanoic acid is selected from the group consisting of:
   2-hydroxypropanoic acid,
   2-hydroxyhexanoic acid,
   2-hydroxyoctanoic acid and
   mixtures thereof.

3. The emulsion of claim 1, wherein the 2-hydroxyalkanoic acid salt is chosen from the sodium, potassium and triethanolamine salts.

4. The emulsion of claim 1, wherein the amount of the skin benefit agent is from 0.1 to 10% by weight of the emulsion.

5. The emulsion of claim 1, wherein the amount of polyoxyethylene-21-stearyl ether is from 0.5 to 10% by weight of the emulsion.

6. The emulsion of claim 1, wherein the emollient oil is selected from the group consisting of:
   polyoxypropylene-15-stearyl ether
   dimethylpolysiloxanes
   lanolin
   cetyl alcohol
   stearyl alcohol
   wheatgerm oil
   isopropyl myristate
   cetyl palmitate
   evening primrose oil
   arnica oil
   avacado oil
   caprylic and capric triglycerols
   ozokerite wax, and
   mixtures thereof.

7. The emulsion of claim 1, wherein the amount of the emollient oil is from 1 to 60% by weight of the emulsion.

8. The emulsion of claim 1, which further comprises a secondary emulsifier selected from the group consisting of: polyoxyethylene-2-stearyl ether polyoxyethylene-2-cetyl ether, and a mixture thereof.

9. The emulsion of claim 1, which further comprises a delivery enhancer selected from the group consisting of:
   butane-1,3-diol,
   glycerol
   propane-1,4-diol,
   dibutyl sebacate, and
   mixtures thereof.

10. The emulsion of claim 1, which further comprises a perfume.

* * * * *